United States Patent [19]

Steuernagel

[11] Patent Number: 4,948,917

[45] Date of Patent: Aug. 14, 1990

[54] PROCESS FOR THE PREPARATION OF BETA-CHLOROETHYLSULFONYLARYL ISOCYANATES

[75] Inventor: Hans H. Steuernagel, Kelkheim, Fed. Rep. of Germany

[73] Assignee: Hoechst Aktiengesellschaft, Frankfurt am Main, Fed. Rep. of Germany

[21] Appl. No.: 479,660

[22] Filed: Feb. 14, 1990

[30] Foreign Application Priority Data

Feb. 16, 1989 [DE] Fed. Rep. of Germany ....... 3904592

[51] Int. Cl.$^5$ ............................................ C07C 119/48
[52] U.S. Cl. ..................................... 560/347; 570/261
[58] Field of Search ......................... 560/347; 570/261

[56] References Cited

U.S. PATENT DOCUMENTS 3,419,542  12/1968  Meininger et al. .
3,518,245   6/1970  Meininger et al. .
4,387,057   6/1983  Schwindt ............................ 560/347

Primary Examiner—Alan Siegel

[57] ABSTRACT

Process for the preparation of β-chloroethylsulfonylaryl isocyanates of the formula (1)

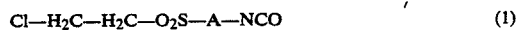

$$Cl-H_2C-H_2C-O_2S-A-NCO \quad (1)$$

wherein A is a phenylene radical, which can contain substituents from the series comprising alkyl($C_1$–$C_6$), alkoxy($C_1$–$C_6$), chlorine, bromine and nitro, or a naphthylene radical, by allowing at least 2 moles of phosgene to act on 1 mole of β-hydroxyethylsulfonyl-arylamine of the formula (2)

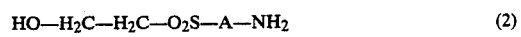

$$HO-H_2C-H_2C-O_2S-A-NH_2 \quad (2)$$

wherein A has the abovementioned meaning, in the presence of a catalyst at temperatures of about 100° to 200° C., if appropriate in an inert solvent.

6 Claims, No Drawings

PROCESS FOR THE PREPARATION OF BETA-CHLOROETHYLSULFONYLARYL ISOCYANATES

DESCRIPTION

The present invention relates to an advantageous process for the preparation of β-chloroethylsulfonylaryl isocyanates of the general formula (1)

$$Cl-H_2C-H_2C-O_2S-A-NCO \quad (1)$$

in which A is an arylene radical, such as, for example, a phenylene radical, which can contain substituents from the series comprising alkyl($C_1$–$C_6$), alkoxy($C_1$–$C_6$), chlorine, bromine and nitro, or a naphthylene radical, by allowing at least 2 moles of phosgene to act on 1 mole of β-hydroxyethylsulfonyl-arylamines of the general formula (2)

$$HO-H_2C-H_2C-O_2S-A-NH_2 \quad (2)$$

in which A has the abovementioned meaning, in the presence of a catalyst at temperatures of about 100° to about 200° C., preferably about 130° to about 180° C., if appropriate in an inert solvent.

Examples which may be mentioned of amines of the general formula (2) are
1-amino-4-(β-hydroxyethylsulfonyl)-benzene,
1-amino-3-(β-hydroxyethylsulfonyl)-benzene,
1-amino-2-methoxy-5-(β-hydroxyethylsulfonyl)-benzene,
1-amino-2-methoxy-4-(β-hydroxyethylsulfonyl)-benzene,
1-amino-4-methoxy-5-(β-hydroxyethylsulfonyl)-benzene,
1-amino-2-methyl-5-(β-hydroxyethylsulfonyl)-benzene,
1-amino-2-methyl-4-(β-hydroxyethylsulfonyl)-benzene,
1-amino-4-methyl-5-(β-hydroxyethylsulfonyl)-benzene,
1-amino-2-methoxy-5-methyl-4-(β-hydroxyethylsulfonyl)-benzene,
1-amino-2,5-dimethoxy-4-(β-hydroxyethylsulfonyl)-benzene,
1-amino-2,4-dimethoxy-5-(β-hydroxyethylsulfonyl)-benzene,
1-amino-2-methyl-5-methoxy-4-(β-hydroxyethylsulfonyl)-benzene,
2-chloro-1-amino-5-(β-hydroxyethylsulfonyl)-benzene,
2-chloro-1-amino-4-(β-hydroxyethylsulfonyl)-benzene,
2-bromo-1-amino-4-(β-hydroxyethylsulfonyl)-benzene,
4-chloro-1-amino-2-methyl-3-(β-hydroxyethylsulfonyl)-benzene,
2-chloro-1-amino-5-methyl-4-(β-hydroxyethylsulfonyl)-benzene,
5-chloro-1-amino-2-methoxy-4-(β-hydroxyethylsulfonyl)-benzene,
2-nitro-1-amino-5-(β-hydroxyethylsulfonyl)-benzene,
1-amino-5-(β-hydroxyethylsulfonyl)-naphthalene,
1-amino-6-(β-hydroxyethylsulfonyl)-naphthalene,
2-amino-5-(β-hydroxyethylsulfonyl)-naphthalene,
2-amino-6-(β-hydroxyethylsulfonyl)-naphthalene and
2-amino-8-(β-hydroxyethylsulfonyl)-naphthalene.

Examples which may be mentioned of suitable catalysts are the dialkyl($C_1$–$C_6$)-amides of aliphatic carboxylic acids having 1 to about 20 carbon atoms, such as, for example, dimethylformamide, diethylformamide, dimethyl-acetamide, diethyl-acetamide, diisobutyl-acetamide, coconut fatty acid dimethylamide or coconut fatty acid diethylamide, and furthermore cyclic compounds having a carboxamide grouping, such as, for example, N-alkyl($C_1$–$C_6$)-pyrrolidones, such as, for example, N-methyl-pyrrolidone or N-ethyl-pyrrolidone, and furthermore phosphoric acid trisdialkyl($C_1$–$C_6$)-amides, such as, for example, phosphoric acid tris-dimethylamide or phosphoric acid tris-diethylamide, dialkyl($C_1$–$C_6$)-alkyl($C_{10}$–$C_{18}$)-phosphine oxides, such as, for example, dimethyl-dodecyl-phosphine oxide, tetraalkyl($C_1$–$C_6$)-ureas, such as, for example, tetramethylurea or tetraethylurea, and furthermore tertiary bases, such as, for example, trialkyl($C_1$–$C_6$)-amines, such as, for example, trimethylamine or triethylamine, and pyridine.

The catalyst can be added before or after the phosgene is added. However, it should be added before the reaction mixture is heated up to the reaction temperature.

It is advantageous to use phosgene in an excess, it being expedient for about 2.5 to about 7 moles, particularly expediently about 4 to about 6 moles, of phosgene to be allowed to act on 1 mole of the amine of the above formula (2).

The preparation of the reaction mixture, including the introduction of 2 to about 4 moles of phosgene per mole of the amine, is carried out at temperatures from about −10° to about +60° C. The reaction mixture is then brought to the intended reaction temperature within the temperature ranges stated above. Additional phosgene can be added in the course of the heating-up phase, up to a maximum total amount of about 7 moles of phosgene per mole of the amine.

Examples of suitable inert solvents are monochlorobenzene and o-dichlorobenzene. If the reaction according to the invention is carried out in an inert solvent which has a boiling point, under normal pressure, below the required maximum temperature, such as, for example, monochlorobenzene, where the mixture is heated up to more than 132° C., a pressure autoclave is advantageously used, it being possible for the gases split off (hydrogen chloride and carbon dioxide) to escape through a valve under suitable pressure control.

When the reaction has ended, excess phosgene is removed and recovered by passing dry air or dry nitrogen through the isocyanate solution formed or by being distilled off.

The waste gases formed (hydrogen chloride and carbon dioxide) may entrain phosgene, which can be recovered from the waste gases by freezing.

The isocyanates of the above formula (1) formed, which are obtained in a high yield, can be isolated in bulk by distilling off the entire solvent. Depending on the solubility of the particular isocyanate, the isocyanate which has precipitated as crystals can also be filtered off after the reaction solution, which has been concentrated to a smaller volume if appropriate, has been cooled.

The isocyanates of the above formula (1) can be employed for reactions both in bulk and in the form of the reaction solution obtained, if appropriate after concentration to a smaller volume.

The isocyanates of the above formula (1) are useful starting substances in the preparation of dyestuffs. Their use for the preparation of reactive dyestuffs is described, for example, in DE-AS 1,289,930.

The following examples serve to illustrate the invention without limiting it thereto. The parts mentioned herein are parts by weight and the percentage data denote percentages by weight, unless noted otherwise. Parts by weight bear the same relation to parts by volume as the kilogram to the liter.

EXAMPLE 1

300 parts of phosgene are passed into a suspension of 201 parts of 1-amino-3-(β-hydroxyethylsulfonyl)-benzene in 1,950 parts of o-dichlorobenzene at 0° to 10° C., while stirring. The mixture is stirred for 20 hours, without further cooling, during which the temperature may be allowed to rise to 20° to 25° C. 5 parts of dimethylformamide are then added and the temperature of the reaction mixture is increased to 175° to 180° C. in the course of 4 hours. A further 200 parts of phosgene are passed into the reaction mixture during the heating up. When the boiling point is reached, the supply of phosgene is discontinued.

The mixture is kept at the boiling point for a further 30 minutes and is then allowed to cool, and the solution is blown free of phosgene by passing in dry air or dry nitrogen. The solution formed contains 220 parts of the isocyanate of the formula

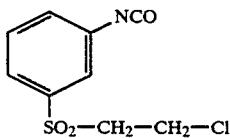

which, in the pure state, has a melting point of 83° C. It can be obtained in bulk by completely distilling off the solvent in vacuo.

However, the isocyanate formed can also be used directly for chemical reactions in the form of the solution obtained, if appropriate after concentration to a lower volume.

EXAMPLE 2

300 parts of phosgene are passed into a suspension of 201 parts of 1-amino-3-(β-hydroxyethylsulfonyl)-benzene in 1,660 parts of chlorobenzene at 0° to 20° C. The mixture is stirred for 6 hours, without further cooling, during which the temperature may be allowed to rise to 30° C. 5 parts of dimethylformamide are now added. The mixture is subsequently heated to the boiling point (132° C.) in the course of 6 hours, while passing in a further 300 parts of phosgene, and is stirred at 132° C. for 14 hours. The waste gas consisting of hydrogen chloride and carbon dioxide is passed through a refrigerated (−30° C.) intensive cooler, in which entrained phosgene condenses and is recovered. The reaction mixture is then freed from excess phosgene by distillation under normal pressure. The solution which remains contains 200 parts of isocyanate of the formula

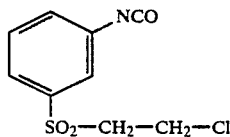

which can be obtained in bulk by distilling off the entire solvent.

EXAMPLE 3

50 parts of 1-amino-3-(β-hydroxyethylsulfonyl)-benzene are stirred in 420 parts of chlorobenzene in a glass autoclave of 1,000 parts by volume capacity. 75 parts of phosgene are passed in at 0° to 10° C. and the mixture is stirred at 10° to 25° C. for 22 hours. 5 parts of dimethylformamide are then added. The temperature of the reaction mixture is then increased to 125° C. in the course of 4 hours, while passing in a further 70 parts of phosgene, after which the supply of phosgene is ended. After the valves have been closed, the temperature is increased to 160° C. in the course of 1 hour and is kept at 160° C. for a further 4 hours.

During this procedure, the waste gas valve is opened so that the pressure in the autoclave does not exceed 2.5 bar. A dry stream of nitrogen is then passed through the solution under normal pressure at 100° C. until the solution is free from residues of phosgene. The solution which remains contains 200 parts of isocyanate of the formula

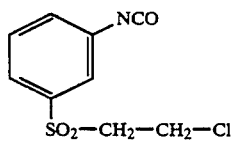

EXAMPLE 4

If the 5 parts of dimethylformamide in Example 3 are replaced by 5 parts of N-methyl-pyrrolidone and the procedure is otherwise as described in Example 3, a solution which contains 210 parts of the isocyanate of the formula shown in that example is obtained.

EXAMPLE 5

If the 5 parts of dimethylformamide in Example 3 are replaced by 5 parts of pyridine and the procedure is otherwise as described in Example 3, a solution which contains 200 parts of the isocyanate of the formula shown in that example is obtained.

EXAMPLE 6

If the 5 parts of dimethylformamide in Example 3 are replaced by 5 parts of dimethylacetamide and the procedure is otherwise as described in Example 3, a solution which contains 200 parts of the isocyanate of the formula shown in that example is obtained.

EXAMPLE 7

If the 5 parts of dimethylformamide in Example 3 are replaced by 5 parts of diisobutyl-acetamide and the procedure is otherwise as described in Example 3, a solution which contains 190 parts of the isocyanate of the formula shown in that example is obtained.

EXAMPLE 8

If the 5 parts of dimethylformamide in Example 3 are replaced by 5 parts of tetramethylurea and the procedure is otherwise as described in Example 3, a solution which contains 180 parts of the isocyanate of the formula shown in that example is obtained.

EXAMPLE 9

A suspension of 50 parts of 1-amino-3-(β-hydroxyethylsulfonyl)-benzene, 420 parts of chlorobenzene and 1.25 parts of N-methyl-pyrrolidone is initially introduced into a glass autoclave of 1,000 parts by volume capacity and 75 parts of phosgene are passed in at 0° to 10° C. The temperature of the reaction mixture is then increased to 128° C. in the course of 4½ hours, while passing in a further 75 parts of phosgene. The supply of phosgene is then discontinued and the valves are closed. The temperature is now increased to 160° C. in the course of one hour and is kept at 160° C. for a further 4 hours. During this, the waste gas valve is opened so that the pressure in the autoclave does not exceed 2.5 bar. Thereafter, dry nitrogen is passed through the solution under normal pressure at 100° C. until the solution contains no more phosgene. The solution which remains contains 210 parts of the isocyanate of the formula shown in Example 3.

EXAMPLE 10

If 2.5 parts of N-methyl-pyrrolidone are employed in Example 9 instead of 1.25 parts and the procedure is otherwise as described in Example 9, the same result as in Example 9 is obtained.

EXAMPLE 11

If the 5 parts of dimethylformamide in Example 1 are replaced by 5 parts of dimethyl-dodecyl-phosphine oxide and the procedure is otherwise as described in Example 1, the isocyanate of the formula shown in Example 1 is obtained in a similarly good yield.

EXAMPLE 12

If the 5 parts of dimethylformamide in Example 1 are replaced by 7 parts of triethylamine and the procedure is otherwise as described in Example 1, the isocyanate of the formula shown in Example 1 is obtained in a similarly good yield.

EXAMPLE 13

If the 5 parts of dimethylformamide in Example 1 are replaced by 5 parts of phosphoric acid tris-dimethylamide and the procedure is otherwise as described in Example 1, the isocyanate of the formula shown in Example 1 is obtained in a similarly good yield.

If 1-amino-3-(β-hydroxyethylsulfonyl)-benzene in Examples 1 to 13 is replaced by the equivalent amount of an amine of the formula (2) listed in column 2 of the following table and the procedure is otherwise in the general sense as described in Examples 1 to 13, the isocyanates of the formula (1) shown in column 3, having the melting points of the pure compounds listed in column 4, are obtained in yields similar to those in Examples 1 to 13.

| Example | Amine of the formula (2) ($R_1 = SO_2$—$CH_2CH_2$—OH) | Isocyanate of the formula (1) ($R_2 = $ —$SO_2$—$CH_2CH_2$—Cl) | Melting point |
|---|---|---|---|
| 14 | 2-OCH$_3$, 5-CH$_3$, 4-R$_1$, 1-NH$_2$ benzene | 2-OCH$_3$, 5-CH$_3$, 4-R$_2$, 1-NCO benzene | 130° C. |
| 15 | 1-NH$_2$, 2-OCH$_3$, 4-R$_1$ benzene | 1-NCO, 2-OCH$_3$, 4-R$_2$ benzene | 122° C. |
| 16 | 2-OCH$_3$, 5-OCH$_3$, 4-R$_1$, 1-NH$_2$ benzene | 2-OCH$_3$, 5-OCH$_3$, 4-R$_2$, 1-NCO benzene | 104° C. |
| 17 | 2-H$_3$CO, 5-R$_1$, 1-NH$_2$ benzene | 2-H$_3$CO, 5-R$_2$, 1-NCO benzene | 76° C. |
| 18 | 1-NH$_2$, 2-Cl, 4-R$_1$ benzene | 1-NCO, 2-Cl, 4-R$_2$ benzene | 103° C. |

-continued

| Example | Amine of the formula (2) ($R_1$ = $SO_2$—$CH_2CH_2$—OH) | Isocyanate of the formula (1) ($R_2$ = —$SO_2$—$CH_2CH_2$—Cl) | Melting point |
|---|---|---|---|
| 19 | $R_1$—[benzene with NO₂ and NH₂ ortho] | $R_2$—[benzene with NO₂ and NCO ortho] | 101° C. |
| 20 | $R_1$—[benzene with NH₂ and CH₃ ortho] | $R_2$—[benzene with NCO and CH₃ ortho] | 89° C. |
| 21 | $R_1$—[benzene with Cl, NH₂, Cl] | $R_2$—[benzene with Cl, NCO, Cl] | 97° C. |
| 22 | $R_1$—[benzene with Br, NH₂] | $R_2$—[benzene with Br, NCO] | 119° C. |
| 23 | $R_1$—[benzene with CH₃, NH₂, Cl] | $R_2$—[benzene with CH₃, NCO, Cl] | 120° C. |
| 24 | $R_1$—[benzene]—NH₂ | $R_2$—[benzene]—NCO | 100° C. |
| 25 | [benzene with $R_1$ ortho to NH₂] | [benzene with $R_2$ ortho to NCO] | 193° C. |
| 26 | [naphthalene with NH₂ and $R_1$] | [naphthalene with NCO and $R_2$] | 130° C. |

I claim:

1. A process for the preparation of a β-chloroethylsulfonylaryl isocyanate of the formula (1)

$$Cl—H_2C—H_2C—O_2S—A—NCO \quad (1)$$

in which A is an arylene radical, which can contain substituents from the series comprising alkyl($C_1$–$C_6$), alkoxy($C_1$–$C_6$), chlorine, bromine and nitro, or a naphthylene radical, which comprises allowing at least 2 moles of phosgene to act on 1 mole of a β-hydroxyethylsulfonyl-arylamine of the formula (2)

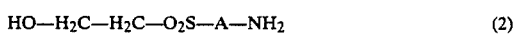
$$HO—H_2C—H_2C—O_2S—A—NH_2 \quad (2)$$

in which A has the abovementioned meaning, in the presence of a catalyst at temperatures of about 100° to about 200° C., if appropriate in an inert solvent.

2. The process as claimed in claim 1, wherein a dialkyl($C_1$–$C_6$)-amide of an aliphatic carboxylic acid having 1 to about 20 carbon atoms, an N-alkyl($C_1$–$C_6$)-pyrrolidone, a phosphoric acid tris-dialkyl($C_1$–$C_6$)-amide, a dialkyl($C_1$–$C_6$)-alkyl($C_{10}$–$C_{18}$)-phosphine oxide, a tetraalkyl($C_1$–$C_6$)-urea, a trialkyl($C_1$–$C_6$)-amine or a cyclic tertiary base is used as the catalyst.

3. The process as claimed in claim 1, wherein dimethylformamide, diethylformamide, dimethyl-acetamide, diethyl-acetamide, diisobutylacetamide, coconut fatty acid dimethylamide, coconut fatty acid diethylamide, N-methylpyrrolidone, N-ethylpyrrolidone, phosphoric acid tris-dimethylamide, phosphoric acid tris-diethylamide, dimethyl-dodecylphosphine oxide, tetramethylurea, tetraethylurea, trimethylamine, triethylamine or pyridine is used as the catalyst.

4. The process as claimed in claim 1, wherein the phosgene is allowed to act on the amine at temperatures of about 130° to about 180° C.

5. The process as claimed in claim 1, wherein the reaction is carried out in monochlorobenzene or o-dichlorobenzene as the inert solvent.

6. The process as claimed in claim 1, wherein if the reaction is carried out in an inert solvent having a boiling point, under normal pressure, below 180° C., a pressure autoclave is used.

* * * * *